United States Patent [19]

Dreikorn

[11] 4,140,778

[45] Feb. 20, 1979

[54] N-PYRIDYL-N-PHENYLAMINES AS RODENTICIDES

[75] Inventor: Barry A. Dreikorn, Indianapolis, Ind.

[73] Assignee: Eli Lilly and Company, Indianapolis, Ind.

[21] Appl. No.: 816,551

[22] Filed: Jul. 18, 1977

[51] Int. Cl.$^2$ ............................................. A01N 9/22
[52] U.S. Cl. ...................................... 424/263; 424/84
[58] Field of Search ................................. 424/263, 84

[56] References Cited

U.S. PATENT DOCUMENTS

| | | | |
|---|---|---|---|
| 2,911,756 | 11/1959 | Geary | 424/84 |
| 3,325,355 | 6/1967 | Goodhue | 424/84 |
| 3,926,611 | 12/1975 | Tomlin et al. | 424/263 |

*Primary Examiner*—V. D. Turner
*Attorney, Agent, or Firm*—Kathleen R. S. Page; Arthur R. Whale

[57] ABSTRACT

Certain substituted N-pyridyl-N-phenylamines as rodenticides.

5 Claims, No Drawings

N-PYRIDYL-N-PHENYLAMINES AS RODENTICIDES

SUMMARY OF THE INVENTION

The present invention is directed to methods employing and compositions comprising certain N-pyridyl-N-phenylamines as rodenticides. The N-pyridyl-N-phenylamines are compounds of the formula

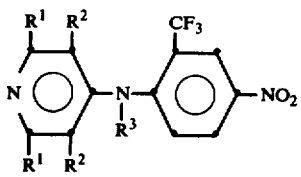

In the above and succeeding formulae, $R^1$ represents in both locations the same halo selected from the group consisting of bromo, chloro and fluoro; $R^2$ represents in both locations the same halo (1) when $R^1$ represents bromo or fluoro, selected from the group consisting of bromo, chloro, and fluoro; and (2) when $R^1$ represents chloro, selected from the group consisting of chloro and fluoro; and $R^3$ represents H or methyl.

The compounds of the foregoing formula are prepared in conventional procedures, such as those taught in U.S. Pat. No. 3,926,611. A preferred synthetic route is the reaction of a halopyridine

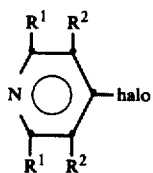

with 4-nitro-2-trifluoromethylaniline:

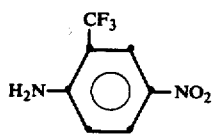

in the presence of an HCl acceptor, conveniently sodium hydride. Preferably the reaction is carried out in an inert solvent and at temperatures of from −10 to +30° C. The $R^3$=methyl compounds are prepared by methylation of the corresponding $R^3$=hydrogen compounds.

4-Nitro-2-trifluoromethylaniline is commercially available. The various halopyridines are known compounds.

Representative compounds to be employed in accordance with the present invention include the following:
N-(2,3,5,6-tetrachloro-4-pyridyl)-N-(4-nitro-2-trifluoromethylphenyl)amine
N-(2,3,5,6-tetrabromo-4-pyridyl)-N-(4-nitro-2-trifluoromethylphenyl)amine
N-(2,3,5,6-tetrafluoro-4-pyridyl)-N-(4-nitro-2-trifluoromethylphenyl)amine
N-(3,5-dichloro-2,6-difluoro-4-pyridyl)-N-(4-nitro-2-trifluoromethylphenyl)amine
N-(2,6-dibromo-3,5-difluoro-4-pyridyl)-N-(4-nitro-2-trifluoromethylphenyl)amine
N-(2,6-dichloro-3,5-difluoro-4-pyridyl)-N-(4-nitro-2-trifluoromethylphenyl)amine
N-(3,5-dibromo-2,6-difluoro-4-pyridyl)-N-(4-nitro-2-trifluoromethylphenyl)amine
N-(2,6-dibromo-3,5-dichloro-4-pyridyl)-N-(4-nitro-2-trifluoromethylphenyl)amine
N-(2,3,5,6-tetrachloro-4-pyridyl)-N-(4-nitro-2-trifluoromethylphenyl)-N-methylamine
N-(3,5-dichloro-2,6-difluoro-4-pyridyl)-N-(4-nitro-2-trifluoromethylphenyl)-N-methylamine Preferred compounds are those of the formula

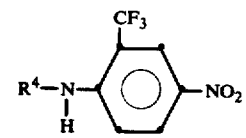

wherein $R^4$ represents 2,3,5,6-tetrachloro-4-pyridyl; 2,3,5,6-tetrafluoro-4-pyridyl; or 3,5-dichloro-2,6-difluoro-4-pyridyl.

The synthesis of the compounds serving as active agent in accordance with the present invention is illustrated by the following examples.

EXAMPLE 1

PREPARATION OF N-(2,3,5,6-TETRACHLORO-4-PYRIDYL)-N-(4-NITRO-2-TRIFLUOROMETHYLPHENYL)AMINE

Sodium hydride (4.8 grams of 57% oil dispersion) was washed with pentane and 30 ml. of DMF was added under nitrogen. The slurry was stirred and cooled to 0° C. To this was added a solution of 4-nitro-2-trifluoromethylaniline (11.0 grams, 0.053 mole) in 20 ml. of DMF; the addition was carried out slowly, keeping the temperature of the reaction mixture below 10° C. The reaction mixture was stirred for one hour, slowly reaching room temperature. The reaction mixture was then cooled to 0° C., pentachloropyridine (10 grams; 0.059 mole) added, and the reaction mixture stirred for 72 hours, slowly reaching room temperature. A yellow solid crystallized. It was separated and recrystallized from ethanol. Elemental analysis showed:

Calc.: C, 34.20; H, 0.95; N, 9.98; Cl, 33.73. Found: C, 34.35; H, 1.01, N, 9.92; Cl, 33.68.

The identity of the product was also confirmed by NMR.

EXAMPLE 2

PREPARATION OF N-(2,3,5,6-TETRAFLUORO-4-PYRIDYL)-N-(4-NITRO-2-TRIFLUOROMETHYLPHENYL)AMINE

Sodium hydride (2.0 grams of 50% oil dispersion) was washed with pentane, filtered, and cooled to 0° C. A solution of 4-nitro-2-trifluoromethylaniline (6.1 grams; 0.030 mole) in 25 ml. of DMF was added over a five-minute period. The reaction mixture was allowed to stir for one hour, the temperature rising as high as 10° C. The reaction mixture was then cooled back down to 0° C. and pentafluoropyridine (5.0 grams; 0.030 mole) in 25 ml. of DMF was added. The reaction mixture was allowed to stir without further cooling for about sixteen hours, then poured over 1.8 liter of crushed ice and the volume adjusted to 1.8 liter with water. A precipitate formed and was allowed to remain in the reaction mixture for about twenty-four hours. The precipitate was then separated by filtration. It was recrystallized from ethanol, yielding 2.6 grams of a first crop (m.p. 104°–5° C.; U.S. Pat. No. 3,926,611 reports 107.7–108) and 3.0 grams of a second crop. Elemental analysis of the first crop showed Calc.: C, 40.58; H, 1.14; N, 11.83. Found: C, 40.34; H, 1.36; N, 11.83.

The identity of the product was also confirmed by IR and NMR.

EXAMPLE 3
PREPARATION OF N-(2,3,5,6-TETRACHLORO-4-PYRIDYL)-N-(4-NITRO-2-TRIFLUOROMETHYLPHENYL)-N-METHYLAMINE

N-(2,3,5,6-Tetrachloro-4-pyridyl)-N-(4-nitro-2-trifluoromethylphenyl)amine (2.0 grams; 0.005 mole), 30 ml. of acetone, 6.0 grams of sodium carbonate and 6 ml. of dimethyl sulfate were mixed and refluxed. After 2 hours, TLC showed no evidence of product. After 8 hours, TLC showed evidence of some product formation. After about sixteen hours, the reaction mixture was quenched by adding water, heating for one hour, and then allowing to cool. Product precipitated and was separated by filtration. It was purified by passing it through a silica gel column with toluene as eluent. Yield was 0.31 gram, m.p. 152°–155° C. Elemental analysis showed Calc.: C, 35.89; H, 1.39; N, 9.66. Found: C, 35.69; H, 1.65; N, 9.65.

The compounds serving as active agent in accordance with the present invention can be used in the same general ways in which known rodenticidal agents are used. Fundamentally, the present invention is directed to a method of reducing a rodent population which comprises supplying to a locus frequented by said population a rodenticidally-effective amount of the present active agent.

The term "rodent" refers most broadly to an animal of the class Mammalia, order Rodentia. The present invention is useful for the control of rodents in this broad sense. However, some rodents can be beneficial, or at least not undesirable. The rodents which are generally undesirable are of the families Muridae and Cricetidae. The family Muridae includes such species as the house mouse (*Mus musculus*), the Norway (or brown or common) rat (*Rattus norvegicus*), and *Rattus rattus*, of which there are several sub-species: the black rat (*R.r. rattus*), the roof rat (*R.r. frugivorus*), and *R.r. alexandrinus*. The family Cricetidae includes such species as the white-footed (or deer) mouse (*Peromyscus leucopus*), the pack rat (e.g. *Neotoma cinerea*), and the meadow mouse (e.g., *Microtus pennsylvanicus*).

As is true of known rodenticidal agents, the present active agent is supplied in a form suitable for ingestion by rodents. The compounds can be formulated in water intended to serve as drinking water. A surface active dispersing agent can be used. Where the compounds are formulated with an inert carrier, such composition can be employed as a "tracking powder"; such a powder is dusted on a surface over which rodents walk, so that the rodents consume the composition when they clean themselves. The compounds can also be formulated as part of a suitable foodstuff. Suitable adjuvants for this purpose include nutritive substances such as oatmeal, ground corn, corn oil, ground oats, soybean products, wheat products, dried skimmed milk, animal fat, salts such as calcium carbonate, dicalcium phosphate, and sodium chloride; trace minerals such as manganese sulfate, zinc carbonate, ferrous sulfate, copper oxide, potassium iodide, and calcium carbonate; vitamins; and sweetening substances such as sugar, molasses, honey, and artificial sweeteners. Suitable adjuvants also include those substances recognized by rodents as attractants-- including not only nutritive substances but also sex hormones and the like. Solid compositions can be offered in finely divided form or compacted as pellets or granules. Typically, concentrations of the present active agent from 50 to 10,000 ppm, preferably 100 to 1000 ppm, have been found to be effective.

Rodents are most attracted to foodstuffs affording a sense of sweetness equivalent to about 5%, by weight, of sucrose. Therefore, a preferred formulation for implementing the methods of the present invention is a rodenticidal bait comprising (1) a grain,
(2) a sweetening agent of sweetness equivalent to from 3 to 7%, by weight, of sucrose, and
(3) the present rodenticidal agent, in a concentration of from 0.005 to 1.0%, by weight, and most preferably in a concentration of from 0.01 to 0.1%, by weight.

The grain can be, for example, wheat, corn, oats, or the like; it can be whole, ground, or the like; and it can be a natural grain or a processed form of the same.

The sweetening agent need not be sucrose, as many other substances are commonly employed in rodenticidal formulations to supply the desired sense of sweetness. Such other substances include honey, molasses, corn syrup, and the like. Therefore, the sweetening agent can be 3–7%, by weight, of sucrose or some other sweetening agent or mixture of agents which is equivalent in sweetness to 3–7% sucrose.

These preferred formulations are ideally adapted to implement the rodenticial methods of the present invention.

The following examples illustrate the present invention and will enable those skilled in the art to practice the same.

EXAMPLE 4
RODENTICIDAL FORMULATIONS

A standard animal feed of the following composition:

| Ingredients | Percent | Lbs./Ton |
|---|---|---|
| Corn, Yellow, Ground | 42.275 | 845.5 |
| Oat groats, rolled | 10.0 | 200.0 |
| Wheat Middlings | 10.0 | 200.0 |
| Soybean Oil Meal, Solvent Extracted Dehulled, 50% | 18.0 | 360.0 |
| Skimmed Milk, Dried | 5.0 | 100.0 |
| Corn, Distillers Dried Solubles | 2.5 | 50.0 |
| Alfalfa Meal, Dehydrated, 17% | 2.5 | 50.0 |
| Whey, Whole Dried | 1.0 | 20.0 |
| Fish Meal with Solubles | 4.0 | 80.0 |
| Animal Fat, Beef Tallow | 2.0 | 40.0 |
| Dicalcium Phosphate, Feed Grade | 0.5 | 10.0 |
| Calcium Carbonate | 1.0 | 20.0 |
| Salt | 0.3 | 6.0 |
| Trace Mineral Premix AN-03 | 0.2 | 4.0 |
| Vitamin Premix CK-1 | 0.5 | 10.0 |
| Vitamin E Premix | 0.1 | 2.0 |

-continued

| Ingredients | Percent | Lbs./Ton |
|---|---|---|
| Methionine Hydroxy Analog (HYDAN) | 0.125 | 2.5 |
| Total | 100.00 | 2000.0 | was employed. Each compound to be evaluated was added to a portion of the standard animal feed in specified concentration. In this manner, three rodenticidal formulations were prepared containing N-(2,3,5,6-tetrachloro-4-pyridyl)-N-(4-nitro-2-trifluoromethylphenyl)amine (200 ppm., 100 ppm., and 50 ppm.); and two rodenticidal formulations were prepared containing N-(2,3,5,6-tetrachloro-4-pyridyl)-N-(4-nitro-2-trifluoromethylphenyl)-N-methylamine (200 ppm. and 100 ppm.).

EXAMPLE 5

RODENTICIDAL EVALUATION

Rats of the *Rattus norvegicus*, Spraque-Dawley albino strain, male, each weighing 50–60 grams, were employed. Control rats were maintained on the standard animal feed described in Example 4. Compounds to be evaluated were formulated also as described in Example 4. Control rats and rats to be treated were randomly assigned. Each group contained 5 rats. Feeding of the respective diet was ad libitum. Consumption per rat per day was checked, except on weekend days, and the rats were weighed and usually necropsied at death or termination of the experiment (generally, day 10). In addition, the rats were observed to determine the day of death.

The results were as reported below. Each line represents data on an individual rat. Symbols are used with the following meanings:

d = day of death
IH = intestinal hemorrhage
TH = lung (thoracic) hemorrhage

In summary, the results reported in Table I show that all of the treated rats succumbed of sub-acute toxicity.

TABLE 1

| Compound | Concentration of compound in diet | Grams of Feed Consumed per day of experiment | | | | | | | | | | Total feed consumed | Weight Change in grams | Necropsy Results |
|---|---|---|---|---|---|---|---|---|---|---|---|---|---|---|
| | | 1 | 2 | 3 | 4 | 5 | 6 | 7 | 8 | 9 | 10 | | | |
| Evaluation I | | | | | | | | | | | | | | |
| N-(2,3,5,6-tetrachloro-4-pyridyl)-N-(4-nitro-2-trifluoromethylphenyl)amine | 200 ppm. | 1 | $1^d$ | | | | | | | | | 2 | −11 | IH |
| | | 2 | $0^d$ | | | | | | | | | 2 | −15 | TH, IH |
| | | 2 | $0^d$ | | | | | | | | | 2 | −10 | IH |
| | | 1 | $1_d$ | $0^d$ | | | | | | | | | 2 | −23 | TH,IH |
| | | 2 | $0^d$ | | | | | | | | | 2 | −12 | IH |
| -(Control) | — | 11 | 12 | 11 | 13 | | | 43 | 15 | 16 | 14 | 135 | 50 | NN |
| | | 8 | 12 | 13 | 14 | | | 44 | 17 | 17 | 17 | 142 | 63 | NN |
| | | 10 | 11 | 12 | 12 | | | 40 | 18 | 16 | 17 | 136 | 70 | NN |
| | | 12 | 11 | 13 | 12 | | | 42 | 18 | 18 | 16 | 142 | 65 | NN |
| | | 10 | 10 | 11 | 13 | | | 40 | 15 | 15 | 14 | 128 | 51 | NN |
| Evaluation II | | | | | | | | | | | | | | |
| N-(2,3,5,6-tetrachloro-4-pyridyl)-N-(4-nitro-2-trifluoromethylphenyl)amine | 100 ppm. | $3_d$ | $2^d$ | | | | | | | | | 5 | −13 | TH,IH |
| | | $4^d$ | | | | | | | | | | 4 | −8 | TH,IH |
| | | 3 | $0^d$ | | | | | | | | | 3 | −11 | TH,IH |
| | | 3 | 1 | 1 | $0^d$ | | | | | | | 5 | −23 | IH |
| | | 3 | 1 | 1 | $0^d$ | | | | | | | 5 | −24 | IH |
| " | 50 ppm. | 6 | 5 | 4 | 4 | | $6^d$ | | | | | 25 | −28 | IH |
| | | 5 | 3 | 2 | 4 | $3^d$ | | | | | | 17 | −28 | IH |
| | | 0 | 2 | 2 | 2* | $2^d$ | | | | | | 8 | −22 | IH |
| | | 7 | 6 | 4 | 4 | $5^d$ | | | | | | 26 | −30 | IH,TH |
| | | 6 | 3 | 3 | 3 | | $7^d$ | | | | | 22 | −31 | IH |
| N-(2,3,5,6-tetrachloro-4-pyridyl)-N-(4-nitro-2-trifluoromethylphenyl)-N-methylamine | 200 ppm. | 3** | $0^d$ | | | | | | | | | 3 | −13 | TH |
| | | $3^d$ | | | | | | | | | | 3 | −5 | IH |
| | | $4^d$ | | | | | | | | | | 4 | −8 | TH,IH |
| | | $4^d$ | | | | | | | | | | 4 | −6 | IH |
| | | 4 | 1 | 0 | 0 | $2^d$ | | | | | | 7 | −21 | TH,IH |
| " | 100 ppm. | 5 | 2 | 3 | 1*** | $0^d$ | | | | | | 11 | −24 | IH |
| | | 6** | $2^d$ | | | | | | | | | 8 | −10 | IH |
| | | 6 | 1 | 1 | $2^d$ | | | | | | | 10 | −22 | IH |
| | | 5 | 2 | 1 | 2 | $0^d$ | | | | | | 10 | −20 | IH |
| | | 4** | 2 | 2 | $1^d$ | | | | | | | 9 | −20 | IH |
| -(Control) | — | 11 | 10 | 12 | 11 | | | 55 | 13 | 12 | | 124 | 59 | NN |
| | | 12 | 11 | 12 | 10 | | | 53 | 14 | 11 | | 123 | 60 | NN |
| | | 11 | 12 | 13 | 12 | | | 62 | 15 | 14 | | 139 | 67 | NN |
| | | 11 | 11 | 12 | 13 | | | 58 | 16 | 16 | | 137 | 69 | NN |
| | | 12 | 12 | 13 | 10 | | | 60 | 16 | 13 | | 136 | 66 | NN |

*eyes watering
**protruding eyes
***nose hemorrhage

I claim:

1. A method of reducing a rodent population which comprises supplying to a locus frequented by said population a rodenticidally effective amount of an active agent which is a compound of the formula

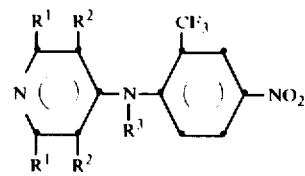

wherein $R^1$ represents in both locations the same halo selected from the group consisting of bromo, chloro, and fluoro; $R^2$ represents in both locations the same halo (1) when $R^1$ represents bromo or fluoro, selected from the group consisting of bromo, chloro, and fluoro, and (2) when $R^1$ represents chloro, selected from the group consisting of chloro and fluoro; and $R^3$ represent H or methyl.

2. The method of claim 1 wherein the active agent is N-(2,3,5,6-tetrachloro-4-pyridyl)-N-(4-nitro-2-trifluoromethylphenyl)amine.

3. The method of claim 1 wherein the active agent is N-(2,3,5,6-tetrachloro-4-pyridyl)-N-(4-nitro-2-trifluoromethylphenyl)-N-methylamine.

4. The method of claim 1 wherein the active agent is N-(2,3,5,6-tetrafluoro-4-pyridyl)-N-(4-nitro-2-trifluoromethylphenyl)amine.

5. The method of claim 1 wherein the active agent is N-(3,5-dichloro-2,6-difluoro-4-pyridyl)-N-(4-nitro-2-trifluoromethylphenyl)amine.

* * * * *